US007083814B2

(12) United States Patent
Ilic et al.

(10) Patent No.: US 7,083,814 B2
(45) Date of Patent: Aug. 1, 2006

(54) ANTIVIRAL SUBSTANCES FROM PLANT CUTICULAR AND EPICUTICULAR MATERIAL

(75) Inventors: Nebojsa Ilic, Highland Park, NJ (US); Ilya Raskin, Manalapan, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 10/401,912

(22) Filed: Mar. 28, 2003

(65) Prior Publication Data

US 2003/0206974 A1 Nov. 6, 2003

Related U.S. Application Data

(63) Continuation-in-part of application No. 09/665,036, filed on Sep. 19, 2000.

(51) Int. Cl.
*A61K 35/78* (2006.01)
(52) U.S. Cl. ...................... 424/765; 424/725
(58) Field of Classification Search ............. 424/195.1, 424/725, 765
See application file for complete search history.

(56) References Cited

U.S. PATENT DOCUMENTS

| 4,594,412 A | 6/1986 | Kitagawa .................... 536/18.5 |
| 4,871,540 A | 10/1989 | Kojima et al. ........... 424/195.1 |
| 5,130,133 A | 7/1992 | Rajagopalan et al. ..... 424/195.1 |
| 5,411,733 A | 5/1995 | Hozumi et al. ........... 424/195.1 |
| 5,534,280 A | 7/1996 | Welch ......................... 426/321 |
| 5,750,709 A | 5/1998 | Castor ........................ 546/348 |
| 5,989,556 A | 11/1999 | Tsai et al. ................. 424/195.1 |

FOREIGN PATENT DOCUMENTS

WO    WO 96/14064    5/1996

OTHER PUBLICATIONS

Mylonakis et al. Plasma Viral Load Testing in the Management of HIV Infection; American Family Physician, Kansas city, Feb. 1, 2001, vol. 63, Iss. 3 pp. 1-6.*
HIV/AIDS Monitoring; Improved HIV Viral Load Test Approved by FDA; Blood Weekly, Atlanta Sep. 26, 2002, pp. 1-2.*
Archer et al. Kelthane Residues on Gravenstein Apples and Pomace-Application and Removal; Journal of Animal Science (1971), 33 (6) pp. 1327-1331.*
Sal'kova et al. Natural Antioxidants in the Coating of the Apple, and Their Isolation and Chromatographic Separation; Applied Biochemistry and Microbiology (1981), 17 (2) pp. 219-224.*
Banerjee, "Therapeutic Trial Of A Group Of Indigenous Plant Extracts In Recurrent Herpes Progenitalis," *Indian J. Dermat.*, 20(2):36-38 (Jan. 1975).

Beuscher et al., "Antiviral activity of African medicinal plants," *J. Ethnopharmacology*, 42:101-109 (Apr. 1994).
Brown, *Tom Brown's Guide to Wild Edible and Medicinal Plants*, The Berkley Publishing Group, New York, New York, pp. 28-29 (1985).
Cutler et al., eds., "The Plant Cuticle," *Linnean Society Symposium Series No. 10, The Linnean Society of London*, Academic Press, New York, 1982 (Table of Contents only).
Debiaggi et al., "Antiviral Activity Of *Chamaecyparis Lawsoniana* Extract: Study With Herpes Simplex Virus Type 2," *Microbiological*, 11:55-61 (1988).
Dimitrova et al., "Antiherpes effect of *Melissa officinalis* L. Extracts," *Acta Microbiologica Bulgarica*, 29:65-72 (1993).
Elanchezhiyan et al., "Antiviral properties of the seed extract of an Indian medicinal plant, *Pongamia pinnata*, Linn., against herpes simplex viruses: in-vitro studies on Vero cells," *J. Med. Microbiol.*, 38:262-264 (1993).
Ferrea et al., "In vitro activity of a *Combretum micranthum* extract against herpes simplex virus types 1 and 2," *Antiviral Research*, 21:317-325 (1993).
Hayashi et al., "Scopadulcic Acid B, a New Tetracyclic Diterpenoid From *Scoparia dulcis* L. Its Structure, $H^+,K^+$-Adenosine Triphosphatase Inhibitory Activity And Pharmacokinetic Behaviour In Rats," *Chem. Pharm. Bull.*, 38(10):2740-2745 (1990).
Kurokawa et al., "Antiviral traditional medicines against herpes simplex virus (HSV-1), poliovirus, and measles in vitro and their therapeutic efficacies for HSV-1 infection in mice," *Antiviral Res*: 22:175-188 (1993).
Lajide et al., "Cyclohexadienones-insect growth inhibitors from the folia surface and tissue extracts of *Senecio cannabifolius,*" *Experientia (Basel)*, 52(3):259-263 (1996).
Martin et al., *The Cuticles of Plants*, St. Martin's Press Inc., New York, New York, 1970 (Table of contents only).
Minshi, "An Experimental Study Of Antiviral Action Of 472 Herbs On Herpes Simplex Virus," *Journal of Traditional Chinese Medicine*, 8(3):203-206 (1988).
Nordby et al., "Relationship of Epicuticular Wax Composition of Grapefruit to Chilling Injury," *J. Agric. Food Chem.*, 39:957-962 (1991).
Serkedjieva et al., "Plant Polyphenolic Complex Inhibits The Reproduction Of Influenza And Herpes Simplex Viruses," *Basic Life Sciences*, 59:705-715 (1992).

(Continued)

*Primary Examiner*—Patricia Leith
(74) *Attorney, Agent, or Firm*—Marshall, Gerstein & Borun LLP

(57) ABSTRACT

Substances having antiviral activity against one or more human disease-causing viruses are disclosed. These antiviral substances are obtained from the cuticular and extracuticular layers of plants. Pharmaceutical and nutraceutical formulations comprising the antiviral substances are also disclosed, as are methods of using such formulations to treat viral diseases.

6 Claims, 6 Drawing Sheets

OTHER PUBLICATIONS

Vanden Berghe et al., "Present Status And Prospects Of Plant Products As Antiviral Agents," *Plenary Lectures of the 32nd International Congress on Medicinal Plant Research Antwerp*, Jul. 23-28, 1984, pp. 47-99, Vlietinck et al., eds., Publisher: Wissenschaftliche Verlagsgesellschaft mbH, Stuttgart (1985).

Vlietinck et al., "Screening of hundred Rwandese medicinal plants for antimicrobial and antiviral properties," *J. Ethnopharmacology*, 46:31-47 (1995).

International Search Report dated May 21, 2002, for PCT/US01/29354.

International Preliminary Examination Report dated Apr. 1, 2003, for PCT/US01/29354.

* cited by examiner

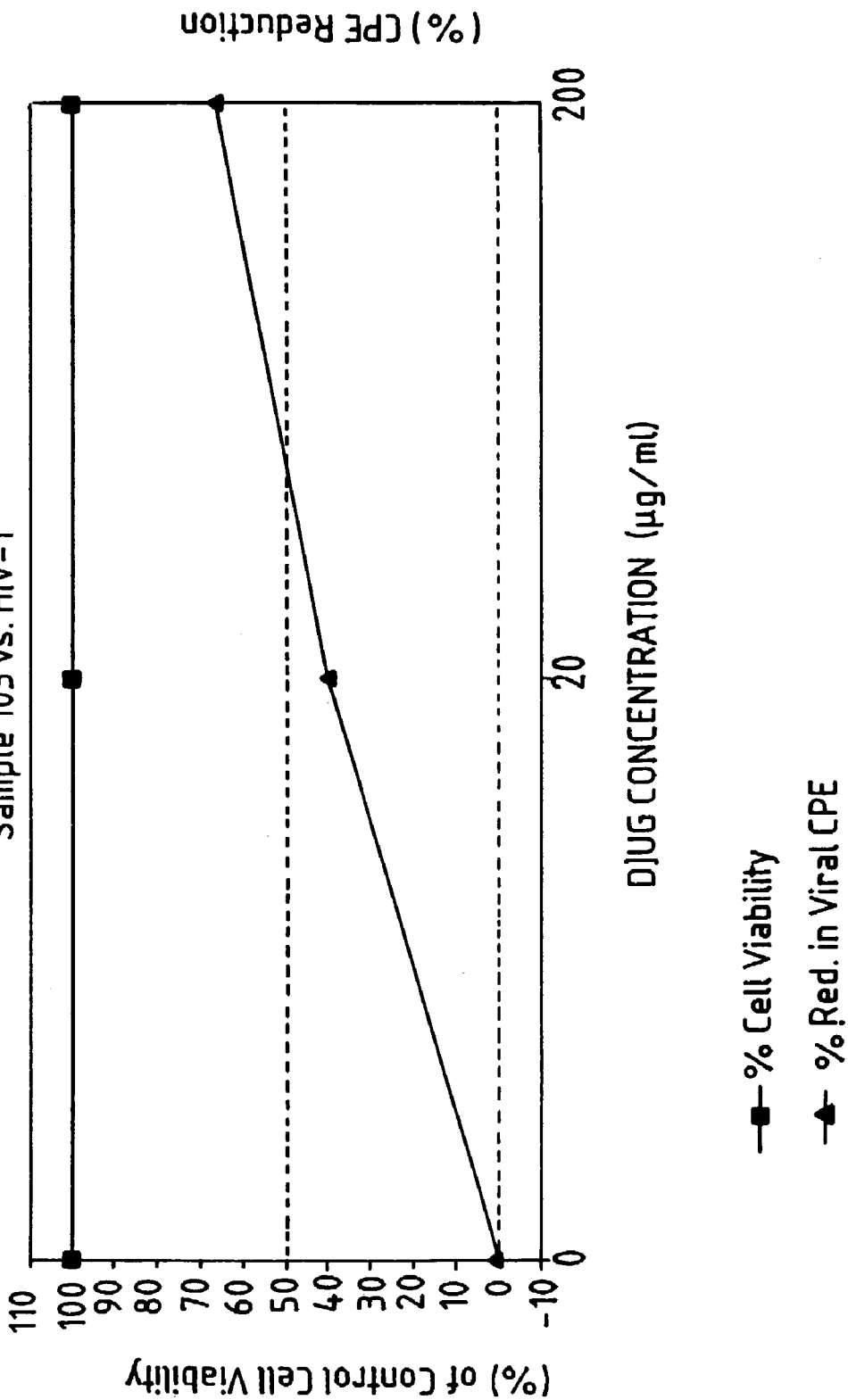

ANTIVIRAL SUBSTANCES FROM PLANT CUTICULAR AND EPICUTICULAR MATERIAL

CROSS REFERENCE TO RELATED APPLICATION

This is a continuation-in-part of U.S. patent application Ser. No. 09/665,036, filed Sep. 19, 2000, the entire disclosure of which is hereby incorporated herein by reference.

FIELD OF THE INVENTION

This invention relates to the field of pharmaceutically active or otherwise beneficial compounds obtained from natural sources. In particular, this invention provides novel, plant-derived substances having activity against a number of viruses that pose serious health concerns.

BACKGROUND OF THE INVENTION

Various scientific articles patent or other publications are referenced throughout the specification. These publications are incorporated by reference herein to describe the state of the art to which this invention pertains.

Long a threat to human health, viral diseases have become a major public health concern in recent decades. Viral pandemics, for example polio and influenza, have been known historically, but the HIV pandemic that arose in the 1980s brought public health concerns about viruses to the forefront of modern research. Besides HIV, other viral diseases are emerging as serious public health concerns, including diseases caused by influenza, hepatitis, herpes viruses and papilloma virus.

Many of the viral diseases appear to be spreading: an example is herpes simplex virus Type 2 (HSV-2), the cause of genital herpes. Recent estimates are that more than 1 in 5 Americans age 12 and older tests seropositive for the HSV Type 2, with approximately 1 million new infections each year.

Statistics like those cited above have helped to spawn massive research efforts into antiviral treatments. Effective antiviral therapeutic agents are sought to combat the viruses mentioned above and many others. The dilemma faced by the researchers is based in the basic biological facts. Viruses, obligate intracellular parasites, while possessing some of their own unique molecular machinery, also rely heavily on cellular metabolism for their propagation. This poses a difficult challenge in that many potential metabolic targets to kill the virus are also toxic or lethal to the host cells, rendering the potential target useless for antiviral therapy.

A safe and effective antiviral agent must interrupt the life-cycle of the virus in some manner, such that the virus cannot replicate adequately, and the compound must have negligible or manageable toxicity to the host cells (or patient). In other words, the antiviral agent must be far more toxic to the virus than to the host cell. Another factor which has come to light relates to the long-term side-effects of certain antivirals, as well as the ability of the viruses to adapt or mutate to negate the effect of certain antiviral agents. Alternatively, more general compounds which boost or modulate immune system responses, such as interferons, may be used in combating viral disease, as may vaccines targeted to specific viruses.

In addition to searching for specific targets for antiviral agents, much research has focused on sources of new lead agents. While rational drug design has been used, in recent years the growth of fields like ethnobotany has been the direct result of the need for new sources of lead drugs. Ethnobotanists, and pharmacologists actively search the plant kingdom for potential active agents, particularly antimicrobial agents, including antiviral compounds.

Antiviral substances from plants are known (Vlietnick et al., 1997, Vanden Berghe et al., 1986). The primary focus of previous work in the field has not been on edible species, but instead on plants known for and used for medicinal purposes in various cultures including Indian (Banerjee, 1975, Elanchezhiyan et al., 1993), African (Beuscher et al., 1994, Ferrea et al, 1993), Bulgarian (Dimitrova et al., 1993, Serkedjieva et al., 1992), Paraguayan (Hayashi et al., 1990), Asian, including Chinese Indonesian and Japanese (Debiaggi et al., 1988, Kurokowa et al., 1993, Zheng, 1988). Methods of obtaining potentially useful plant materials typically has involved grinding or otherwise macerating a selected tissue, then preparing a crude extract from fresh or dried tissue or consuming the tissue directly.

These same studies have examined tissues from many different parts of the plant and stages of development, ranging from whole plant extracts to extracts from the aerial parts to those more specifically from leaves, stems, twigs, bark, flowers, buds, fruits, peels, seeds, roots, rhizomes, tubers, or bulbs. Thus far no studies have focused solely on substances that exist in the outermost layers of the plant, i.e., the epidermis and cuticle, or on substances deposited onto the surfaces of plants in an "epicuticular" layer.

The cuticle serves as an outer protective layer located external to the epidermis of most if not all plant parts, and consists of several different layers of non-cellular membranes. Peels or rinds as separated from fruits may consist of thickened membranes attached to a layer of epidermal cells. Bark is the most complex form of plant surface covering.

The cuticle is composed primarily of cutin, suberin, waxes and tannins along with a variety of other compounds. Cuticle composition varies from one variety of plant to another. The biosynthetic pathways leading to the complex compounds present are highly involved with many biosynthetic intermediates and alternate pathways present. Each component, such as the tannins or the waxes, may consist of a multitude of compounds, for example, apple wax contains well over 50 compounds including hydrocarbons, saturated and unsaturated fatty acids, primary and secondary alcohols, diols and hydroxy acids (Martin and Juniper, 1970; Cutler et al., 1982).

As to the spectrum of activity for plant-derived antivirals, many different viruses have been challenged with extracts of whole plants or various plant parts. Examples of viruses tested include HIV, polio virus, hepatitis, herpes viruses, such as HSV-1, HSV-2, cytomegalovirus and measles virus, influenza, rhinovirus, parainfluenza, vesicular stomatitis virus (VSV), vaccinia virus (VV), encephalitis, and African Swine Fever virus. Of the most frequently tested viruses, HSV-1 and HSV-2 have been challenged with numerous plant extracts. Some of the extracts have shown activity against these viruses, while others have not.

The field of plant-derived antiviral preparations is represented in the patent literature. U.S. Pat. No. 5,750,709 teaches a method for isolating therapeutic compositions from natural source materials in which the material is first de-waxed, de-fatted or de-oiled via supercritical fluid extraction. The de-fatted material is then further extracted to obtain the natural therapeutic composition. U.S. Pat. No. 4,871,540 teaches a process of producing an immune-modulating substance from the tissue of *Zea mays*. The substance is identified as a glycolipid and is expected to be useful in treating various disorders including asthma, rhinitis, hepatitis and AIDS and other disorders where an immuno-modulating substance would be effective. U.S. Pat. No. 5,411,733 claims methods for treating various viral diseases with a variety of plant extracts based on traditional medicinal plants. According to the teachings provided in this patent, the extracts were obtained via water or methanol extraction, as opposed to non-polar solvents. The compounds isolated were further subjected to and stable to boiling for 10 minutes. Presumably, they used the knowledge of the plants' traditional medicinal uses to identify which portions of the plant to use for preparation of the extracts. Most recently, U.S. Pat. No. 5,989,556 teaches compositions of plant extracts derived from traditional Chinese herbal medicines and useful in treating animals infected with hepatitis B, hepatitis C or HIV. The compositions taught therein are primarily mixtures of powdered herbs or water-based extracts or suspensions of these herbs and herb mixtures. They also teach a water-based extract which is subjected to and stable to boiling. They hypothesized that the active component was soluble in neutral aqueous solution; it was not soluble in alcohols, or common organic solvents, including hexane. The inventors suggest that the active component may be a simple organic acid.

Despite the amount of research and prior art, given the exemplary statistics cited above on the prevalence and rate of spread of HSV, antivirals from any source whatever, with low toxicity are needed to develop novel, safe and effective treatments for this disease.

SUMMARY OF THE INVENTION

In accordance with the present invention, substances from the cuticular or epicuticular layers of plants have been identified and are shown to possess potent antiviral activities. Also provided are methods for obtaining these antiviral substances from the cuticular and epicuticular material of plants. When prepared according to the method taught, these substances have particular therapeutic application for herpes simplex virus HIV, influenza virus and other viral infections. In addition, the invention also provides methods for the use of these substances in a therapeutic mode.

As used herein, the term "cuticle" or "cuticular layer" refers to a substantially non-cellular multi-layered structure that lies over and merges into the outer walls of epidermal cells, as shown diagrammatically in FIG. 3 (taken from Martin & Juniper, *The Cuticle of Plants,* St. Martin's Press, New York 1970). The term "cuticular material" refers simply to material that is obtained from any part of the cuticle. Likewise, it is known that substances (such as waxes) are exuded from the cuticle onto the outermost surface of the plant, forming a layer referred to herein as the "epicuticular layer". The term "epicuticular material" refers to material or substances obtained from this layer.

It should also be understood that the term "substance" or "agent" when used herein in the singular is intended to encompass the plural as well. For example, a cuticular or extracuticular antiviral substance may contain a single substance, or it may contain a mixture of two or more substances.

According to one aspect of the present invention, an antiviral preparation obtained from the cuticular and/or epicuticular material of plants comprising substances soluble in an organic solvent, but not requiring disruption of the plant cells interior to the epidermal layer, is provided. In one embodiment, the active materials are localized externally to the epidermis of the plant, i.e., in the cuticle or deposited onto the surface of the plant in an "epicuticular" layer. The antiviral substances can be found in the cuticular and epicuticular layers of different plant parts, including but not limited to fruits, flowers, leaves, stems and roots. In a preferred embodiment, plant parts containing these antiviral agents are obtained from one or more readily available plant species, such as apple, avocado, bearberry, black cherry, blueberry, cabbage, cherry, cork oak, cucumber, eucalyptus, grape, holly, orange, pear, plum (including Japanese plum), rhododendron, tobacco, tomato, wax palm and willow, to name a few.

According to another aspect of the invention, a method for obtaining of an antiviral preparation from the cuticular and epicuticular layers of plants, is provided. The objective of the method is to obtain materials contained in the cuticle and epicuticular layers of the plant, while minimizing or eliminating extraction from internal plant tissues. The method comprises the following steps: (a) plant tissues (preferably intact, but fruit peels also may be used) are exposed to a solvent which solubilizes the active material located external to the epidermis of the plant (i.e., the cuticle and epicuticular layer) under conditions that leave the internal plant tissues substantially unaffected; (b) the solvent is partly or completely removed, leaving behind the concentrated cuticular and epicuticular material.

The solvent is one that is capable of solubilizing compounds from a matrix of waxy or cuticular material, or compounds dispersed on the plant's surface that are not washed off by rain or dew; typically these would comprise substantially non-polar solvents. For instance, the solvent may be selected from the group consisting of hexane, chloroform, dichloromethane, heptane, ether, petrolether, t-butyl ether, DMSO, long-chain alcohols, petroleum derivatives, supercritical fluids and liquefied gases. The solvent may be removed by evaporation under vacuum, or by filtration, precipitation or lyophilization.

In one embodiment, the concentrated cuticular and epicuticular material is resolubilized or resuspended in a second solvent that, at the concentrations used, is minimally toxic or nontoxic to cells in vitro or organisms in vivo. Appropriate solvents for such purposes include combinations of one or more of ethanol, water, polyethylene glycol, DMSO, glycerol, phenol, and other such solvents. In another embodiment, the antiviral material is suspended in a combination of one or more of the above-mentioned solvents, or in a colloid, or in another medium.

According to another aspect of the present invention, a pharmaceutical formulation comprising an antiviral substance obtained from plant cuticular and epicuticular material is provided. The pharmaceutical formulation of this invention is effective in the treatment of a viral disease process, and especially useful for the treatment of Herpes Simplex Virus Type I, influenza and or HIV infections.

According to another aspect of the present invention, a method for the treatment of, or therapeutic intervention in, a viral disease process is provided. The method comprises administering to a patient the above described pharmaceutical formulation at a frequency and duration sufficient to result in reduction or alleviation of the symptoms or cause of the viral disease process. In a preferred embodiment, the viral disease is caused by HSV, HIV or influenza virus.

Also provided in accordance with the present invention is a nutraceutical formulation comprising the aforementioned antiviral substances obtained from plant cuticular and epicuticular layers. Since the antiviral substances of the present invention can readily be prepared from common food species, it is contemplated herein that such substances can readily be included with formulations of nutraceutical products which are now commonly available and used by millions of health conscious consumers interested in alternative approaches to health. Such nutraceutical products, comprising the antiviral substances include for example, health beverages, herbal drinks, elixirs, juices, or teas, powdered beverage mixes, nutritional supplements, vitamins, additives, natural remedy formulations, health bars, creams, balms, sprays, and the like.

Other features and advantages of the present invention will be better understood by reference to the drawings, detailed description and examples that follow.

BRIEF DESCRIPTION OF THE DRAWINGS

FIGS. 2a, 2b and 2c: Relative Effectiveness of Plant Derived Antiviral Substances Against HIV 1 Infections in CEM-SS Cells. Line graphs showing the % reduction in cytopathic effect (CPE) of HIV-1(triangles, right axis) and the relative cell survival, as a percentage of viability controls (squares, left axis) at each of two concentrations for each sample tested. Concentrations are indicated by numbers (in µg/ml) on horizontal axis. Samples are cuticular and epicuticular substances derived from plants as follows: 95, willow; 102, wax palm; and 105, plum.

DETAILED DESCRIPTION OF THE INVENTION

Figure 1A:
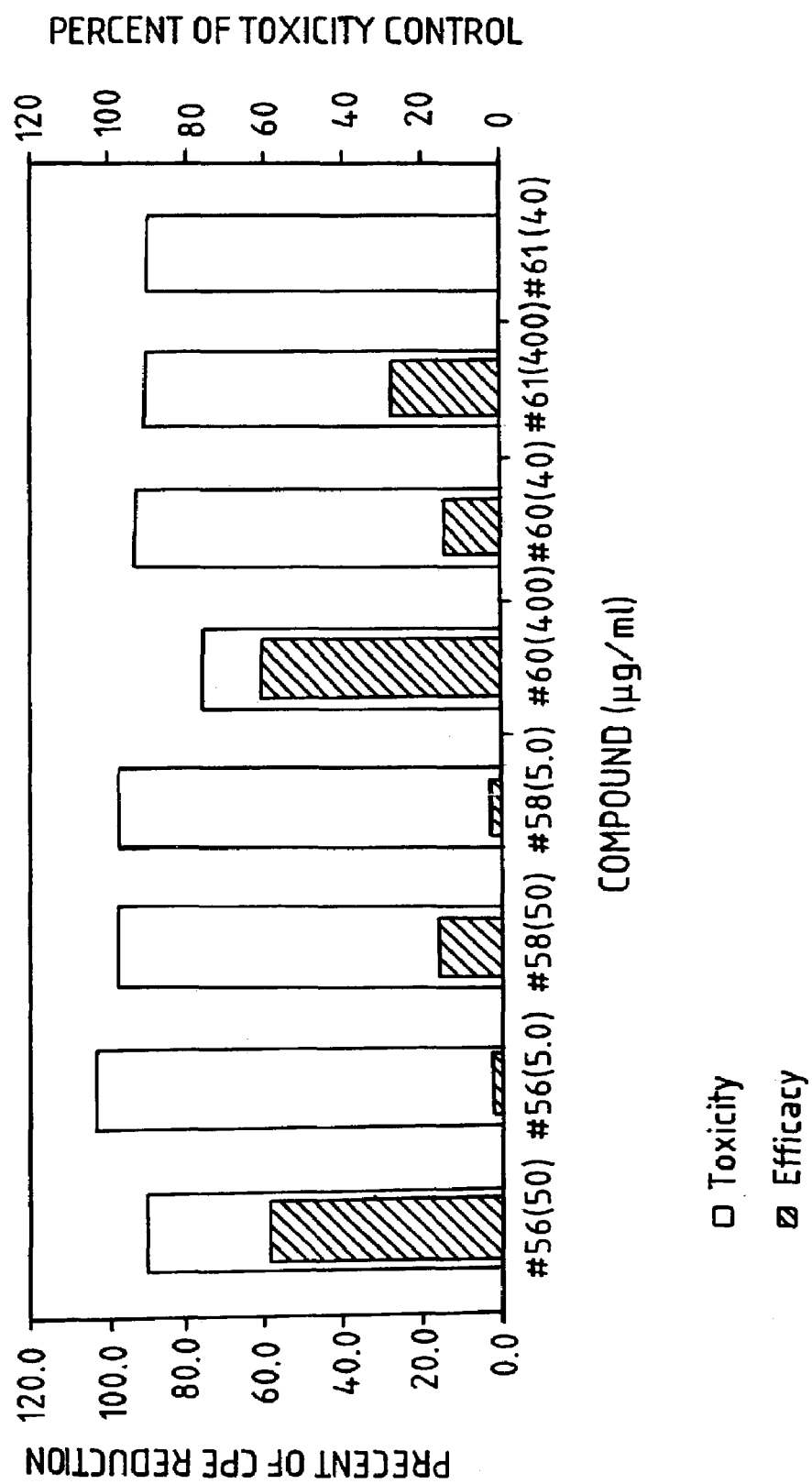
FIGS. 1a and 1b: Relative Effectiveness of Plant-Derived Antiviral Substances Against Herpes Simplex Virus Type 1 HF Infections in Vero Cells. Bar charts showing the % reduction in cytopathic effect (CPE) of HSV-1 (hatched bars, left axis) and the relative cell survival, as a percentage of controls (solid bars, right axis) at each of two concentrations for each sample tested. Concentrations are indicated in parentheses next to sample number on horizontal axis. Samples are cuticular and epicuticular substances derived from plants as follows: 56, pear; 57, blueberry; 58, avocado; 59, cabbage; 60, apple; 61, apple; 62, grape; 64, apple; 65, orange; and 68, tomato.

The development of antiviral substances that are safe and nontoxic to infected cells and yet inhibit the replication of the virus by one or more means is a area of great need and much research. Ethnobotanists, pharmacologists, and others have turned to the natural world, and especially the plant kingdom, as a vast resource of potentially therapeutic agents with such properties as high efficacy and low toxicity. Advances in this area will add greatly to the limited base of therapeutic options for treatment of viral disease processes.

In accordance with the present invention, plant-derived agents possessing antiviral properties are provided. It has been discovered in accordance with the present invention that agents with such desirable therapeutic properties can be removed from the cuticular and epicuticular material present in plants, with minimal disruption of the plant tissue internal to the epidermis of the plant. The antiviral properties of these materials likely arises from one or more constituents which comprises one or more constituents of plant cuticular and epicuticular materials, such as waxes, plant wax components, cutins, terpenoids, triterpenoids, phenolics, primary alcohols, secondary alcohols, hydrocarbons, diketones, fatty acids and flavonoids, to name a few.

Whole plants or intact plant parts may used as a source material of the cuticular and epicuticular material, including fruits, flowers, leaves, roots, stems, and bark. Preferred for use in the present invention are fruits, leaves and stems. These plant parts preferably are intact; however, peels or rinds that are mechanically separated from fruits or other plant parts also may serve as an economical source of cuticular and epicuticular material, inasmuch as such peels or rinds are often discarded as refuse in the processing of fruits and vegetables.

In one embodiment, a plant species is selected which is a readily available agricultural or horticultural plant or crop. Examples include but are not limited to species of plants such as apple (*Malus* spp.), pear (*Pyrus* spp.), grape (*Vita* spp), orange (*Citrus* spp.), tomato (*Lycopersicon esculentum*), cabbage (*Brassica* spp.), cucumber (*Cucumis* spp.), cherry, black cherry, plum, peach and apricot (all *Prunus* spp.), avocado (*Persea* spp.), blueberry (*Vaccinium* spp.) bearberry (*Arctostaphylos* spp.) olive (*Olea*) and wax palm (*Copernicia* spp. or *Ceroxylon* spp). Other examples include tobacco (*Nicotianum* spp.), cork oak (*Quercus occidentalis*), eucalyptus (*Eucalyptus* spp.), rhododendron (*Rhododendron* spp.), holly (*Ilex rotunda*), Japanese plum (*Eriobotrya japonica*) and willow (*Salix* spp.). Still other examples include plants of the following genera: *Euphorbia, Pedilanthus, Syagrus, Cocos, Attalea, Stipa, Glyceria, Saccharum, Myrica, Rhus, Sapium, Linum, Agave, Cannabis, Raphia, Coccus, Ligustrum, Fraxinus, Benincasa, Ricinus, Buxus, Mesembryanthemum, Rubus and Melaleuca*. These genera, as well as certain of the genera listed before these genera, contain species known to produce an abundance of waxy or oily cuticular and epicuticular materials. Preferred plants include apple and tomato.

In one embodiment, tissues are selected which are separate from the main agronomic feature of the plant, for example: stem and leaf tissue from the tomato vine could be used for extraction after the tomato fruit is picked. Alternatively, in the case of fruits and vegetables, those items which due to damage or defect are not usable for the food or feed purpose intended may be used for extraction in lieu of diverting first quality produce. It is also contemplated that the plant tissues from which the antiviral extracts are prepared may consist of a mixture tissues from one or more of these plants in certain combinations as are useful. In addition, as discussed above, the peels or rinds of fruit provide a useful source of cuticular and epicuticular material. These examples are intended to illustrate, not to limit, the invention.

In accordance with the present invention, a method for preparing antiviral substances from cuticular and epicuticular plant materials is provided. The method comprises exposing the plant surfaces to a solvent that solubilizes the cuticular and epicuticular portions of the plant, while leaving the remaining plant tissues substantially intact, followed by concentrating or otherwise preparing the antiviral substances for further use.

As used herein, the term substantially unaffected means the plant or plant part remains substantially intact insofar as there is no required disruption of the plant, plant part, plant tissue or plant cell. Preferably, there is no disruption of the plant, plant part, plant tissue or plant cell. One of ordinary skill would recognize that an insubstantial disruption of the plant, plant part, plant tissue or plant cell (e.g., torn leaves) is within the scope of the disclosed methods and antiviral preparations. One benefit of the disclosed methods and antiviral preparations is realized by exposing the cuticular and epicuticular layers to a solvent. These layers, which are generally disposed on the exterior of plants, are typically available to the solvent without intentional disruption.

The step of solvent exposure typically involves dipping, spraying or otherwise briefly exposing the plant (or plant part) surface to a substantially nonpolar solvent of a type commonly used for dissolving waxes, lipids and similar substances found in the cuticle. An appropriate solvent typically comprises one or more solvents selected from the group consisting of hexane, chloroform, dichloromethane, heptane, ether, petrolether, t-butyl ether, DMSO, and lower aliphatic alcohols, for example, methanol, ethanol, and isopropanol. Other examples of suitable solvents include organic solvents, high molecular-weight alcohols, ethers, petroleum derivatives, supercritical fluids, liquefied gases, and other such solvents as are known to those skilled in the art.

The method includes an optional step of clarification. The clarification step comprises one or more separation steps to remove insoluble material and plant residue from the solubilized cuticular and epicuticular material. Examples of clarification processes include but are not limited to: gravity settling; screening; filtration, for example, through a bed composed of filtration medium such as would be known to those skilled in the art, or mixing of filtration media in bulk with the solubilized extract and allowing the filtration bed to form as the filtration media is separated from the solubilized extract; cross-filtration; and/or centrifugation in either continuous or batch modes under forces large enough to separate the debris from the solubilized extract.

In another embodiment the initial or clarification solvent is removed in order to: (a) remove any potentially deleterious effects of the solvent; and (b) concentrate the antiviral properties of the extracted material. Solvent removal is accomplished by art-recognized methods, including one or more of the following: vacuum removal, evaporation, heating, centrifugal evaporation, rotary evaporation, vortex evaporation, lyophilization, liquid-liquid separation, solid-liquid separation, and/or precipitation of the material followed by separation of the precipitate and the solvent. In one embodiment, solvent is removed via rotary evaporation. In an embodiment preferred for large-scale preparation, removal comprises a continuous evaporation process such as is known in the art. In another embodiment, solvent is removed after precipitation of the antiviral properties. Such precipitation processes are well known in the art, and may include but are not limited to one or more of the following: addition of a precipitant, such as a salt or a further solvent, change in temperature, and/or change in pH. Following precipitation, the liquid phase may be decanted, filtered, evaporated or removed by means as are known to those skilled in the art.

Following solvent removal, the antiviral substances may be redissolved or resuspended in another fluid or matrix. In one embodiment, the antiviral substances are resolubilized in a biologically compatible medium for activity testing. Suitable media for this purpose are those that do not in any way interfere or reduce the activity of the antiviral properties, into which is dissolved the antiviral substances. Appropriate media for resolubilizing or suspending the antiviral substances include combinations of one or more of the following: ethanol, water, polyethylene glycol, DMSO, glycerol, phenol, and other such solvents. The antiviral substances may be suspended in a combination of one or more of the above-mentioned media, or in a colloid, or in another medium capable of retaining the antiviral agents in suspension. In yet another embodiment, the antiviral preparation is used as-is after removal of the initial solvent and formulated into a pharmaceutical or nutraceutical composition. The antiviral may be mixed with an appropriate bulking agent to allow convenient measurement, or alternatively may be directly formulated into a composition. In one embodiment, the antiviral plant material is mixed with the lipid-containing portion or ingredients of the pharmaceutical or nutraceutical being formulated.

One or more of the cuticular and epicuticular antiviral substances described herein have been demonstrated active against HSV-1, HIV-1 and influenza virus, as set forth in greater detail in the examples. These substances may also be used as therapy against other viruses, including but not limited to poliovirus, hepadnaviruses, other herpesviruses, cytomegalovirus, measles virus, rhinovirus, parainfluenzavirus, vesicular stomatitis virus (VSV), vaccinia virus (VV), encephalitis virus, and African Swine Fever virus.

In accordance with the invention, an oral pharmaceutical formulation effective in the treatment of a viral disease process, is provided. The pharmaceutical formulation comprises active ingredients which include the antiviral substances from plant cuticular and epicuticular material. In another embodiment, a topical pharmaceutical formulation is provided, which comprises the plant-derived antiviral substance as a waxy material that can readily mix with lipid-containing or lipid-based ingredients and carriers for application as a balm, ointment, lotion, roll-on, rub, cream or other such topical applications as are known in the art.

Pharmaceutical preparations comprising the antiviral substances are formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of the antiviral substances calculated to produce the desired antiviral effect in association with the selected pharmaceutical carrier. Procedures for determining the appropriate dosage unit are well known to those skilled in the art.

Dosage units may be proportionately increased or decreased based on the weight of the patient. Appropriate concentrations for achieving reduction or elimination of symptoms or viral load may be determined by dosage concentration curve calculations, as known in the art.

Also provided in accordance with the present invention is a method for therapeutic use of the antiviral pharmaceutical formulations of the invention for an intervention in a viral disease process. The method of using the antiviral formulations therapeutically comprises administering a therapeutically effective dose comprising the antiviral pharmaceutical formulation of the invention, at a frequence and for a duration sufficient to reduce or alleviate symptoms of the viral disease, or to lessen viral load. The form of administration includes injection, oral administration, inhalation or aerosolized administration, a 'patch' or transdermal application, a sublingual application, especially if the antiviral formulation is in colloidal form, or a topical application. In one embodiment, the results of the method comprise greatly reduced or eliminated symptoms related to the viral disease process. In a preferred embodiment, the results of the method comprise a patient who is clinically free of the viral disease. In a more preferred embodiment, the results of the method comprise a patient who is clinically free of the disease, and from whom all virus has been eliminated.

Also provided in accordance with the present invention are nutraceutical formulations comprising antiviral substances obtained from the cuticular and epicuticular material of plants. In a preferred embodiment, the substances are obtained from an edible plant. In another embodiment, the substances comprises a waxy material which readily mixes with lipid based ingredients.

The following examples are provided to describe the invention in greater detail. They are intended to illustrate, not to limit, the invention.

EXAMPLE 1

Antiviral Effects of Samples from Cuticular and Epicuticular Layers of Selected Plant Species The following example outlines antiviral evaluations against HIV-1, HSV-1, and HCMV for samples derived from cuticular and epicuticular layers of various plants.

Materials and Methods:

Sample preparation. Samples were prepared by dipping intact plant parts 3–5 minutes in dichloromethane at room temperature, followed by filtration and evaporation of the solvent. The samples were formulated in DMSO and stored at −20° C. prior to assay. Samples were evaluated for antiviral activity at 1:200 and 1:2000 dilution in each assay.

The above sample preparation conditions are exemplary. One of ordinary skill in the art would recognize that the sample preparation conditions may be adjusted depending on the plant or plant part and the selected solvent. For example, the volume, temperature, pressure, exposure duration, and concentration (as measured by percent weight, based on the total weight of the solvent) of the solvent may be varied.

Anti-HSV-1 Cytoprotection Assay. Cell Preparation: In 96-well flat-bottomed tissue culture plates, Vero cells were grown to monolayers using Eagle's Minimum Essential Medium (EMEM) supplemented with 10% heat-inactivated fetal bovine serum (FBS), L-glutamine, penicillin, and streptomycin.

Virus Preparation: The herpes simplex virus type 1 strain HF was used for the assay. A frozen, pretitered aliquot of virus was allowed to thaw slowly to room temperature in a biological safety cabinet.

Plate Format: Antiviral assays tested two dilutions of each sample in duplicate against the challenge virus. Full and proper controls were run simultaneously with the test samples: cell controls containing medium alone; virus-infected controls containing medium and virus; drug cytotoxicity controls containing medium and each control or test sample concentration; reagent controls containing culture medium only (no cells); and colorimetric controls containing controls or test samples and medium, but no cells. The plates were incubated at 37° C., 5% $CO_2$ until maximum cytopathic effect (CPE) was observed in the untreated virus control cultures (approximately day 5).

MTS staining of screening plates: Inhibition of CPE (indicating increased cell viability) was determined by reduction of the formazan dye MTS (Promega) following a 4 hour incubation at 37° C. and measured spectrophotometrically at 490 nm, with 650 nm as the reference wavelength. % CPE reduction of the virus-infected wells and % cell viability of uninfected control wells were calculated.

Data Analysis: Concentration for 50% inhibition of virus replication ($IC_{50}$), Concentration for 50% cytotoxicity ($TC_{50}$) and therapeutic index (TI, $IC_{50}/TC_{50}$) were calculated by linear regression analysis and graphed. The antiherpesvirus drug Acyclovir was used as a relevant positive control.

Anti-HIV-1 Cytoprotection Assay. Cell Preparation: CEM-SS cells were passaged in T-75 flasks for use in the assay. One day prior to assay, the cells were split 1:2 to provide exponential growth at time of infection. Total cell number and viability was determined using a hemocytometer and trypan blue exclusion staining. Only populations with cell viability greater than 95% were utilized for assay. The cells were resuspended at $5 \times 10^4$ cells/ml in tissue culture medium, then added in a volume of 50 μl to the sample-containing plates.

Virus Preparation: The lymphocyte-tropic virus strain, $HIV-1_{RF}$, was obtained from the NIH AIDS Research and Reference Reagent Program. Virus was maintained in CEM-SS cells for the production of virus stocks, which were titered, separated into aliquots and stored at −80° C. Each pretitered aliquot of virus was allowed to thaw slowly to room temperature in a biological safety cabinet. The virus was resuspended in tissue culture medium such that the virus titer contained in 50 μl, and added to each assay well, would result in 85% to 95% cell killing at 6 days post-infection.

Plate Format: A complete set of controls was included with each assay plate: Cell controls containing medium alone; virus-infected controls containing medium and virus; cytotoxicity controls containing medium and each control or test sample concentration; reagent controls containing culture medium only (no cells); and colorimetric controls containing test samples or controls and medium (no cells). In addition, experimental samples wells (wells with cells plus virus plus test sample) were performed in duplicate at two concentrations per test compound.

Data Analysis: Concentration for 50% inhibition of virus replication ($IC_{50}$), Concentration for 50% cytotoxicity ($TC_{50}$) and therapeutic index (TI, $IC_{50}/TC_{50}$) were calculated by linear regression analysis and graphed. AZT was used as a relevant positive control.

Anti-Influenza A Cytoprotection Assay. Cell Preparation: MDCK cells ($2 \times 10^4$ cells/well) were pregrown for 48 h at 37° C. in a 96 well plate. Dulbecco's Modified Eagles Medium: (DMEM) supplemented with 10% heat-inactivated fetal bovine serum, antibiotics, 1% sodium pyruvate, 1% L-glutamine, and 2% nonessential amino acids mixture was used to propagate the cells. The cell monolayer was rinsed twice with PBS prior to addition of control or test samples.

Virus Preparation: Pre titered Influenza A (Vic/3/75 H3N2 strain) was added with test compound using medium containing trypsin 1 mg/ml, and incubated for 3 days at 37° C., 5% $CO_2$.

Plate Format: A complete set of controls was included with each assay plate: Cell controls containing medium alone; virus-infected controls containing medium and virus; cytotoxicity controls containing medium and each control or test sample concentration; reagent controls containing culture medium only (no cells); and colorimetric controls containing control or test samples and medium (no cells). In addition, experimental compounds wells (wells with cells plus virus plus test sample) were performed in duplicate at two concentrations per test compound.

MTS staining of screening plates: Inhibition of CPE (indicating increased cell viability) was determined by reduction of the formazan dye MTS (Promega) following a 4 hour incubation at 37° C and measured spectrophotometrically at 490 nm, with 650 nm as the reference wavelength. % CPE reduction of the virus-infected wells and % cell viability of uninfected control wells were calculated.

Data Analysis: Concentration for 50% inhibition of virus replication ($IC_{50}$), Concentration for 50% cytotoxicity ($TC_{50}$) and therapeutic index (TI, $IC_{50}/TC_{50}$) were calculated by linear regression analysis and graphed. Ribavirin was used as a relevant positive control.

Figure 1B:
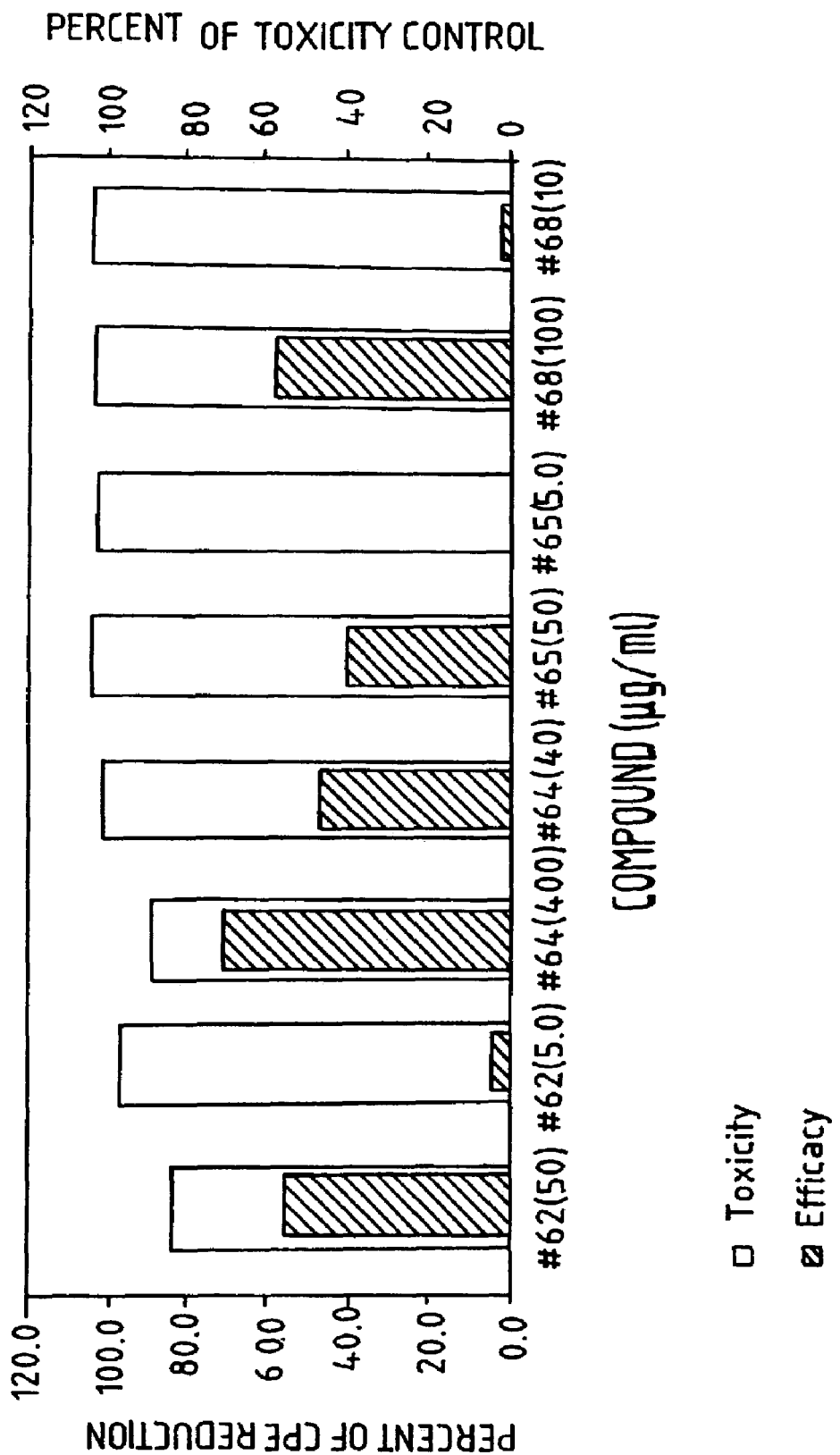

Results:

Anti-HSV-1 activity of the test samples: Extracts were evaluated against the HF strain of HSV-1 in Vero cells. The results are summarized in Table 1. Therapeutic Index (TI) is the calculated ratio of the $IC_{50}/TC_{50}$ and is used to determine relative potency between compounds. The graphical representation presented in FIGS. 1a and 1b show the relationship between the antiviral efficacy (% CPE Reduction) and compound toxicity (% Toxicity Control) expressed as a percent of the relevant control, virus no compound or cells no compound, respectively.

The study indicated several samples (numbers 56 (pear), 60 (apple), 62 (grape), 64 (apple) and 68 (tomato)) produced 50% inhibition of the HF strain of HSV-1, at sample concentrations between 44 mg/ml and 316 mg/ml. The extracts that reached $IC_{50}$ values were not toxic at the highest concentration; therefore, a therapeutic index could not be calculated. Samples 61 (apple) and 65 (orange) did not reach an $IC_{50}$ nor a $TC_{50}$ at the highest concentration tested. Some reduction in cytopathic effect (CPE) was observed at the higher dose, therefore these samples may yield $IC_{50}$ values if tested at higher concentrations. In these experiments, Acyclovir yielded an $IC_{50}$ value of 2.4 mM which falls within acceptable parameters of the assay ($IC_{50}$ values 1–10 μM).

AntiInfluenza Activity of the extracts. Samples did not reach an $IC_{50}$ nor did they show toxicity at the highest concentration tested. Some inhibition was observed at the higher dose, therefore, again due to the fact that the samples are from crude materials rather than purified compounds, these samples will likely yield $IC_{50}$ values if tested at higher concentrations. Samples extracted from, for example, apple, avocado (n particular), tomato and cabbage hold promise in this regard.

TABLE 1

| Sample | Results $IC_{50}$ (μg/ml) | $IC_{50}$ (μg/ml) | TI | Comments |
|---|---|---|---|---|
| 56 obtained from pear fruit (by extraction in dichloromethane) | 43.58 | >50 | >1.147 | 58.1% reduction in CPE at 50 μg/ml with no toxicity |
| 57 obtained from blueberry fruit (by extraction in dichloromethane) | >200 | 100.80 | NA | 9.4% reduction in CPE at 20 μg/ml with no toxicity |
| 58 obtained from avocado fruit (by extraction in dichloromethane) | >50 | >50 | NA | 15.0% reduction in CPE at 50 μg/ml with no toxicity |
| 59 obtained from cabbage leaf (by extraction in dichloromethane) | >50 | >50 | NA | No activity observed |
| 60 obtained from organic apple fruit (by extraction in dichloromethane) | 316.26 | >400 | >1.265 | 60.7% reduction in CPE at 400 μg/ml with no toxicity |
| 61 obtained from organic apple fruit (by extraction in methanol) | >400 | >400 | NA | 27.7% reduction in CPE at 400 μg/ml with no toxicity |
| 62 obtained from grape (fruit) (by extraction in dichloromethane) | 45.06 | >50 | >1.110 | 55.6% reduction in CPE at 50 μg/ml with no toxicity |
| 64 obtained from non-organic apple (by extraction in dichloromethane) | 89.92 | >400 | >4.448 | 70.5% reduction in CPE at 400 μg/ml; 46.7% reduction in CPE at 40 μg/ml; no |
| 65 obtained from orange skin (peel) (by extraction in dichloromethane) | >50 | >50 | NA | 39.8% reduction in CPE at 50 μg/ml with no toxicity |
| 68 obtained from tomato fruit (by extraction in dichloromethane) | 87.54 | >100 | >1.142 | 57.7% reduction in CPE at 100 μg/ml with no toxicity |
| Acyclovir (μM) | 2.4 | >100 | >41.20 | Control |

<sup>a</sup>NA: not applicable

EXAMPLE 2

Antiviral Effects of Additional Test Samples from Cuticular and Epicuticular Layers of Plants The following example outlines antiviral evaluations against HSV-1 and HIV-1, for extracts derived from cuticular and epicuticular layers of plant species.

Materials and Methods:

Test materials were prepared as described in Example 1. The samples samples were formulated in DMSO and stored at −20° C. prior to assay. Samples were evaluated for antiviral activity at 1:200 and 1:2000 dilution in each assay.

Anti-HIV-1 Cytoprotection Assay. Cell preparation, virus preparation and plate format were as described in Example 1.

XTT staining of screening plates: After 6 days of incubation at 37° C. in a 5% $CO_2$ incubator, the test plates were analyzed by staining with the tetrazolium dye, XTT. XTT-tetrazolium is metabolized by the mitochondrial enzymes of the metabolically active cells to form a soluble formazan product, allowing the rapid quantitative analysis of the inhibition of HIV-induced cell killing by anti-HIV test samples. On day 6 post-infection plates were removed from the incubator and observed. The use of round-bottom microtiter plates allows rapid macroscopic analysis of the activity of a given test compound by the evaluation of pellet size. The results of the macroscopic observations were confirmed and enhanced by further microscopic analysis.

XTT solution was prepared daily as a stock of 1 mg/ml in PBS. Phenazine methosulfate (PMS) solution was prepared at 0.15 mg/ml in PBS and stored in the dark at −20° C. XTT/PMS stock was prepared immediately before use by diluting the PMS 1:100 into PBS and adding XTT solution at 40 μl/ml. Fifty μl of XTT/PMS was added to each well of the plate and the plate is reincubated for 4 h at 37° C. Adhesive plate sealers are used in place of the lids, the sealed plate is inverted several times to mix the soluble formazan product and the plate is read spectrophotometrically at 450 nm with a Molecular Devices Vmax plate reader.

Data Analysis: Concentrations for 25%, 50% and 95% inhibition of virus replication ($IC_{25}$, $IC_{50}$, $IC_{95}$); Concentration for 25%, 50%, and 95% cytotoxicity ($TC_{25}$, $TC_{50}$, $TC_{95}$) and antiviral index (AI, $IC_{50}/TC_{50}$) were calculated by linear regression analysis and graphed. AZT was used as a relevant positive control.

Anti-HSV-1 Cytoprotection Assay. Cell Preparation, virus Preparation, plate formatting, MTS staining and data analysis were as described in Example 1.

Results: Results are summarized in Table 2.

TABLE 2

Antiviral Summary

| Sample Number | Sample Identification | Activity Against: HSV-1 | HIV-1 |
|---|---|---|---|
| 95 | Willow | Inactive | TI > 2.3 |
| 102 | Wax Palm | TI > 1.6 | TI > 20 |
| 105 | Plum | Promising | TI > 2.3 |

As can be seen from the table, a number of the samples showed substantial antiviral activity against $HIV-1_{RF}$, HSV-1, or both. In the HIV-1 assay, the samples from willow leaf (95), wax palm (102) and plum (105) all had TI>1.1. Wax palm had the highest TI, that being >20; indicating that it was very effective even at the 10 μg/ml concentration tested.

Figure 2A:
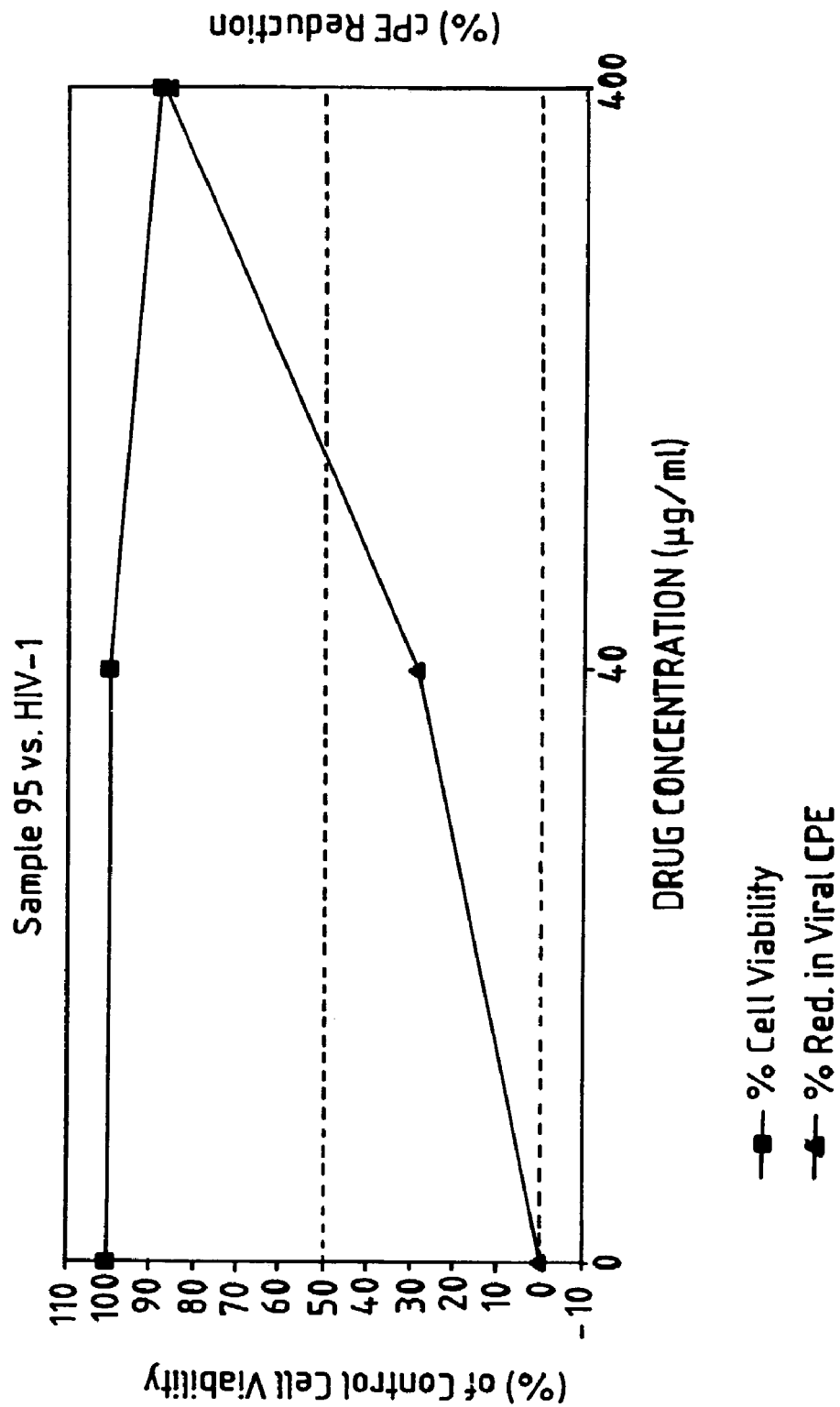
Figure 2B:
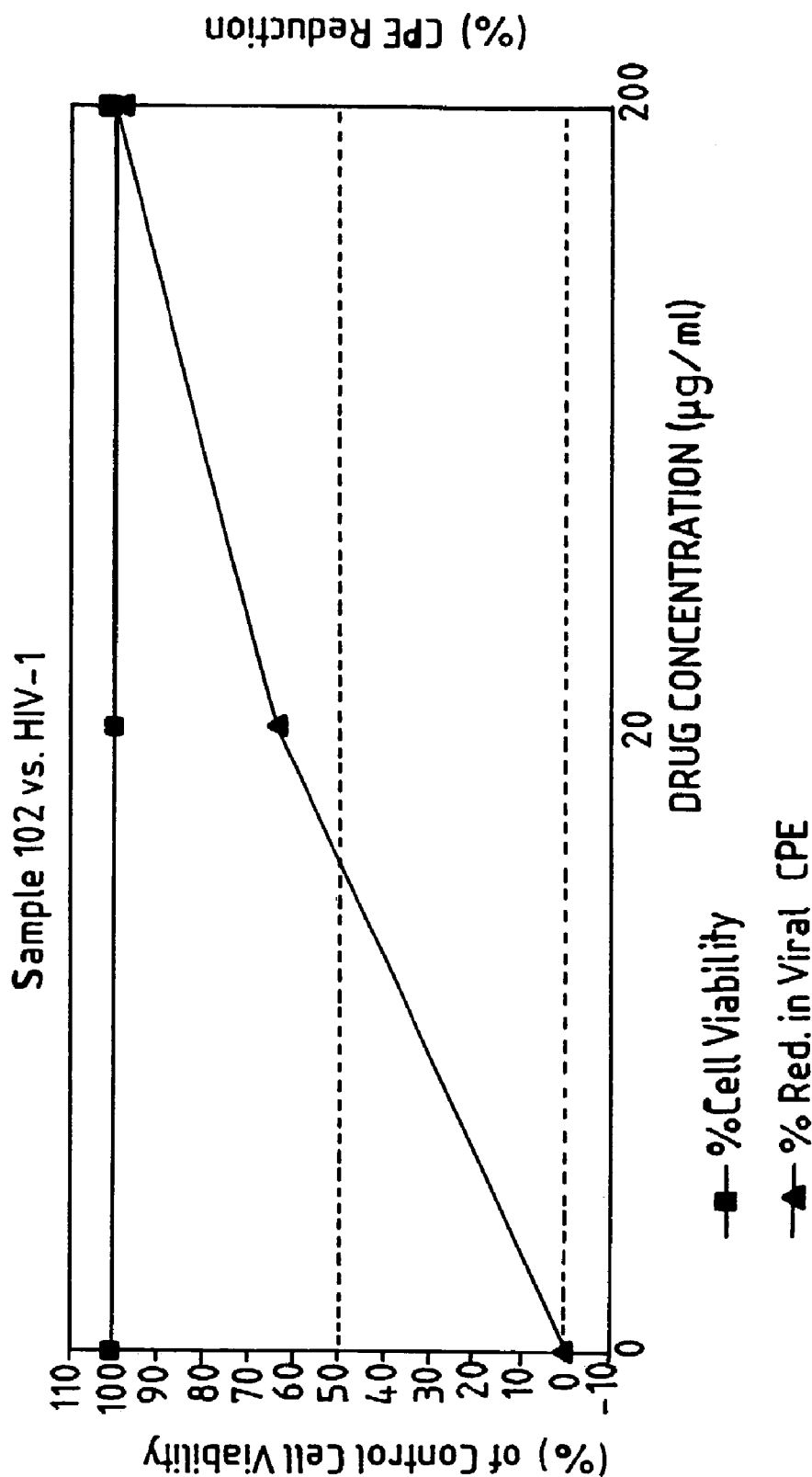
Figure 3:
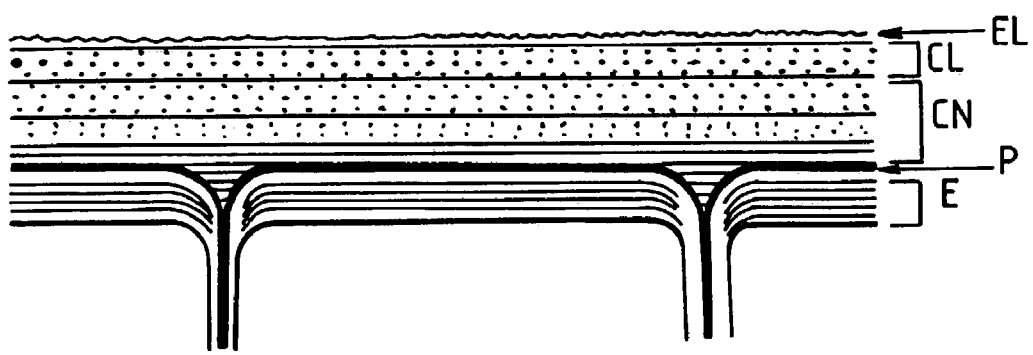
FIG. 3: Line drawing showing cross-section of a typical plant cuticle, indicating cuticular and epicuticular layers from which antiviral substances are obtained. EL=epicuticular layer; CL=cuticularized layer; CN=cutinized layer; P=pectin layer; E=epidermal cell wall.

The data are shown graphed in FIGS. 2a, 2b and 2c. The AZT control gave results within the expected parameters, establishing the validity of the assays.

The results against the HSV-1 virus also proved some compounds active towards this virus. The wax palm sample showed significant antiherpes activity in these assays, the sample from plum showed activity at the higher concentration only, but again since little toxicity was observed even higher concentrations may be tested to gain additional antiviral effect.

The present invention is not limited to the embodiments described and exemplified above. It is capable of variation and modification within the scope of the appended claims.

We claim:

1. A method for producing a composition possessing antiviral activity comprising substances obtained from cuticular or epicuticular layers external to an epidermis of a plant or plant part, the method comprising:
    a) exposing the plant or plant part to a solvent under conditions sufficient to solubilize substances in the cuticular and epicuticular layers of the plant or plant part, while leaving cells and tissues internal to the epidermis substantially unaffected;
    b) obtaining a solution or suspension of plant cuticular and epicuticular substances; and,
    c) formulating the solution or suspension with a pharmaceutically acceptable carrier to form a topical composition possessing antiviral activity in a form selected from the group consisting of a balm, an ointment, a lotion, a roll-on, a rub, and a cream.
   wherein the plant or plant part is selected from the group consisting of Malus.

2. The method according to claim 1, wherein the solvent comprises a compound selected from the group consisting of hexane, chloroform, dichloromethane, heptane, ether, petrolether, t-bulyl ether, DMSO, sup ercritical fluids and carbon dioxide.

3. The method according to claim 1, wherein the step of exposing comprises dipping the plant or plant part into the solvent.

4. The method according to claim 1, wherein the step of exposing comprises spraying the plant or plant part with the solvent.

5. The method according to claim 1, wherein the plant or plant part is an apple fruit peel.

6. A topical antiviral composition prepared by the method of claim 1.

* * * * *

UNITED STATES PATENT AND TRADEMARK OFFICE
CERTIFICATE OF CORRECTION

PATENT NO.       : 7,083,814 B2
APPLICATION NO.  : 10/401912
DATED            : August 1, 2006
INVENTOR(S)      : Ilic et al.

It is certified that error appears in the above-identified patent and that said Letters Patent is hereby corrected as shown below:

In the Claims Col. 14:
In Claim 2, line 36, please delete "sup ercritical", and insert -- supercritical --

Signed and Sealed this

Twenty-ninth Day of April, 2008

JON W. DUDAS
*Director of the United States Patent and Trademark Office*